United States Patent [19]

Blombäck et al.

[11] 4,348,315

[45] Sep. 7, 1982

[54] PROCESS IN PURIFICATION AND CONCENTRATION OF THE FACTOR VIII-COMPLEX

[76] Inventors: E. G. Birger Blombäck; Lars G. Thorell, both of Karolinska Institutet, S-10401 Stockholm, Sweden

[21] Appl. No.: 215,530

[22] Filed: Dec. 11, 1980

[30] Foreign Application Priority Data

Dec. 20, 1979 [SE] Sweden .............................. 7910527

[51] Int. Cl.³ ................................................ A23J 1/06
[52] U.S. Cl. .................................. 260/112 B; 424/101; 424/177
[58] Field of Search .............................. 424/101, 177; 260/112 B

[56] References Cited

U.S. PATENT DOCUMENTS

| | | | |
|---|---|---|---|
| 3,631,018 | 12/1971 | Shanbrom | 260/112 B |
| 3,652,530 | 3/1972 | Johnson | 424/101 X |
| 4,081,432 | 3/1978 | Delente | 424/101 X |
| 4,087,415 | 5/1978 | Bick | 424/101 X |

OTHER PUBLICATIONS

"Arkiv För Kemi", 12, (1958), 36, T. 387–396, (IAP 395, Second Paragraph).

Primary Examiner—Sidney Marantz
Attorney, Agent, or Firm—Cushman, Darby & Cushman

[57] ABSTRACT

A process in purification and/or concentration of factor VIII complex, starting from a preparation of factor VIII complex, obtained and concentrated in a known manner, mostly in the form of a precipitate, such as cryoprecipitate or Cohn's fraction I-0. This preparation is dissolved in a glycine solution of at least 1.5 M at a temperature of at least +15° C. and pH of 6.3-7.8 and a supernatant liquid is recovered as a product or for further working-up.

13 Claims, 4 Drawing Figures

PROCESS IN PURIFICATION AND CONCENTRATION OF THE FACTOR VIII-COMPLEX

BACKGROUND OF THE INVENTION

This invention relates to a process in purification and/or concentration of the factor VIII complex. It is started from a preparation prepared in a manner known per se, in which the factor VIII complex is enriched. The preparation is mostly in the form of a precipitate.

The factor VIII complex is lacking or its activity is reduced in hemophilia of type A and in v. Willebrand's disease. The symptoms in these diseases are often serious bleeding in joints and muscles and from mucous membranes.

The factor VIII complex takes part in the biochemical reactions promoting the coagulation of blood. In the coagulation of blood, an insoluble polymer, fibrin, is formed from a soluble protein, fibrinogen. The reason for the polymerization or formation of fibrin is an enzymatic change of the fibrinogen molecule, which is caused by the enzyme trombin (factor IIa). This enzyme is formed from protrombin (factor II) under the influence of an enzyme, called factor Xa. Said enzyme is also present as a zymogen in the blood before the coagulation. The zymogen form is called factor X. The conversion of factor X to factor Xa also takes place enzymatically by means of an enzyme called factor IXa. The factor VIII complex takes part in this reaction (as a co-factor) together with calcium and phospholipide. In the following scheme the most important reactions in the coagulation (clotting) of blood are illustrated. Totally a great number of various factors take part here.

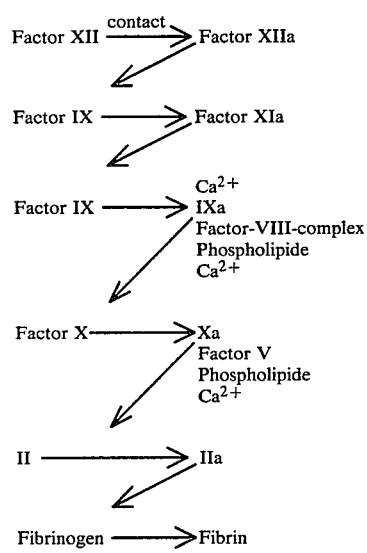

The factor VIII complex consists of at least two components, one of which is called the factor VIII:C, in which C means that this component is responsible for the coagulation activity of the complex in the reaction chain shown. This component is considered to contain the antigen proved by means of antibodies, which are developed in certain persons suffering from hemophilia and which prevent the coagulation activity of factor VIII:C. The antigen is called F VIII:CAG. The other component has been called factor VIII-RAG or F VIII-related antigen. This antigen is different from the antigen F VIII:CAG. The factor VIII:C and the (antigen) factor VIII:CAG are lacking in hemophilia of type A in a serious form. In this disease there is a normal content of factor VIII:RAG. In v. Willebrand's disease, there is a lack of factor VIII:RAG in the blood and a corresponding lack of factor VIII:C. For persons suffering from a serious form of v. Willebrand's disease the lack of factor VIII:RAG is almost total and the content of factor VIII:C is about 5% of the normal content. In v. Willebrand's disease, the activity of the so-called factor VIII:RCF is highly reduced. This activity is an expression of a component in plasma which causes agglutination of trombocytes in the presence of the antibiotic "Ristocetin". It is now considered that the activity of the factor VIII:RCF is an expression of the component or components in plasma which has (have) the factor VIII-related antigen (factor VIII:RAG). The lack of factor VIII:RCF in v. Willebrand's disease has been found to be correlated to the prolonged capillary bleeding time existing in this disease and which is an expression of a defective trombocyte function. This function is normal in hemophilia type A, whereas the coagulation time of the blood is prolonged due to the reduced content of factor VIII:C. In v. Willebrand's disease, the coagulation time is also prolonged as there is also a lack of factor VIII:C in this disease, especially in serious forms thereof. The lack of factor VIII:C in v. Willebrand's disease is considered to be a consequence of the lack of factor VIII:RAG/RCF, which seems to act as carrier molecule for factor VIII:C. In accordance with the existing values, one can illustrate the factor VIII-complex schematically in the following way:

$$\text{F VIII:RAG/RCF} = = \text{F VIII:C/CAG}$$

A number of processes are known at present for the preparation of plasma concentrates for clinical use, which contain the factor VIII complex or parts thereof. The complex can be precipitated from Cohn's fraction I with alcohol. Additional concentration of the complex can be carried out by extraction of inert protein whith about 1 M glycine solution in cold. Fractionation of plasma with ether or tannic acid has also been used for the preparation of factor VIII concentrates. Concentrates prepared by precipitation in cold of the factor VIII complex have been widely used due to the simplicity of the method. In certain cases, polyethylene glycol has been used for precipitation of the factor VIII complex. Variants of the glycine method, in which either other amino acids than glycine have been used or glycine has been used for precipitation of the factor VIII complex are also known.

Concentrates prepared according to the glycine method contain all factors in the factor VIII complex, but the specific activity is low, and therefore great volumes of solution must be injected in the treatment of hemophilia. Preparations with a high specific activity have often been found to lack the factor correcting the prolonged bleeding time in v. Willebrand's disease.

As to the yield of the coagulation active part (F VII:C), this is low in most preparation processes or between 20 and 30% at best.

In the treatment of hemophilia, it is of a great importance to use concentrates of the F VIII complex with a high specific activity of all the factors included in the complex. Hemophilia A as well as v. Willebrand's disease can be treated with such a concentrate. A specific activity which is 200-300 times greater than that in plasma also permits preparations containing the necessary therapeutic dose in a small volume (5-10 ml). This makes the treatment easier as the dose can be administered in an injection syringe. This also makes it possible to carry out the treatment for example at home by the sick person himself as is usual in the treatment of diabetes with insulin.

In most countries, the supply of blood is unsatisfactory in respect of the possibilities of preparing sufficient amounts of factor VIII complex for treatment of hemophilia from available blood volumes. This situation might be considerably improved if the percentage yield of the factor VIII complex could be increased in preparation from blood.

BRIEF DISCLOSURE OF THE DRAWINGS

DETAILED DESCRIPTION OF THE INVENTION

It has now been found to be possible to prepare a highly satisfactory factor VIII complex having a specific activity that is about 150-250 times greater than that in plasma, while the yield is between 40 and 60%. The process according to the invention is charactericed in that the resulting preparation of factor VIII complex is dissolved in a glycine solution of at least 1.5 M at a temperature of at least +15° C. and a pH of 6.3-7.8, preferably pH 6.8, and that supernatant liquid is recovered as a product or for further working-up. The resulting product (factor VIII complex) contains the antihemophilic factor (factor VIII:C/CAG) and the component (factor VIII-RAG/RCF) which is lacking in v. Willebrand's disease.

The starting preparation obtained in a way known per se can be prepared by cryoprecipitation or fractionation of plasma with alcohol. Through the process of the invention, impurities are then precipitated in a glycine solution at and about room temperature and at a neutral pH. In previously known processes, glycine solutions have been used at a low temperature for dissolution of impurities from a precipitated factor VIII complex. Glycine at a concentration of about 2 M has also been used for precipitation of the factor VIII complex from a protein solution at a low temperature.

According to the invention, the preparation of factor VIII complex is now treated at a temperature of at least 15° C., preferably at a temperature of 15°-37° C., such as 20°-35° C., and most preferably at about 30° C.

In doing this, the factor VIII complex remains in solution, while contaminating protein is precipitated. The pH is approximately neutral. The ionic strength of the solution should be between 0.1 and 0.5, calculated as buffer salts. The glycine concentration at the precipitation of impurities can vary between 1.5 M and a saturated solution and is preferably 1.6-2.3 M, such as 1.8-2.2 M, and most preferably about 2.0 M. By this precipitation of protein which is inert in this connection, the specific activity in the supernatant liquid is increased by 2-7 times and the yield is between 80 and 100%.

EXAMPLES OF THE INVENTION

Figure 1:
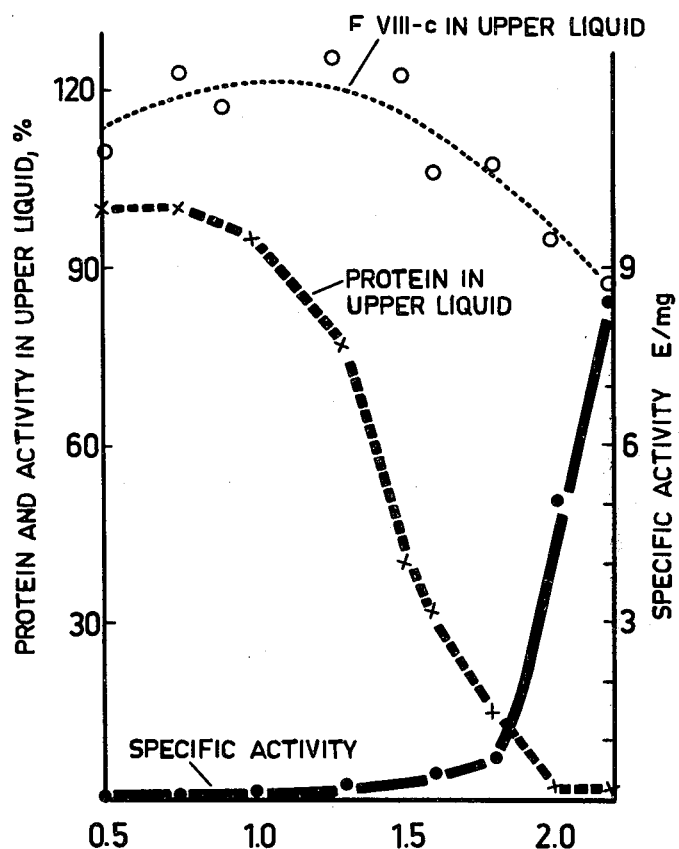
FIG. 1 is a graph showing the protein and activity (left vertical), in percent, of the supernatant liquid and the specific activity (right vertical) as a function of the molarity of the glycine solution.
Figure 2:
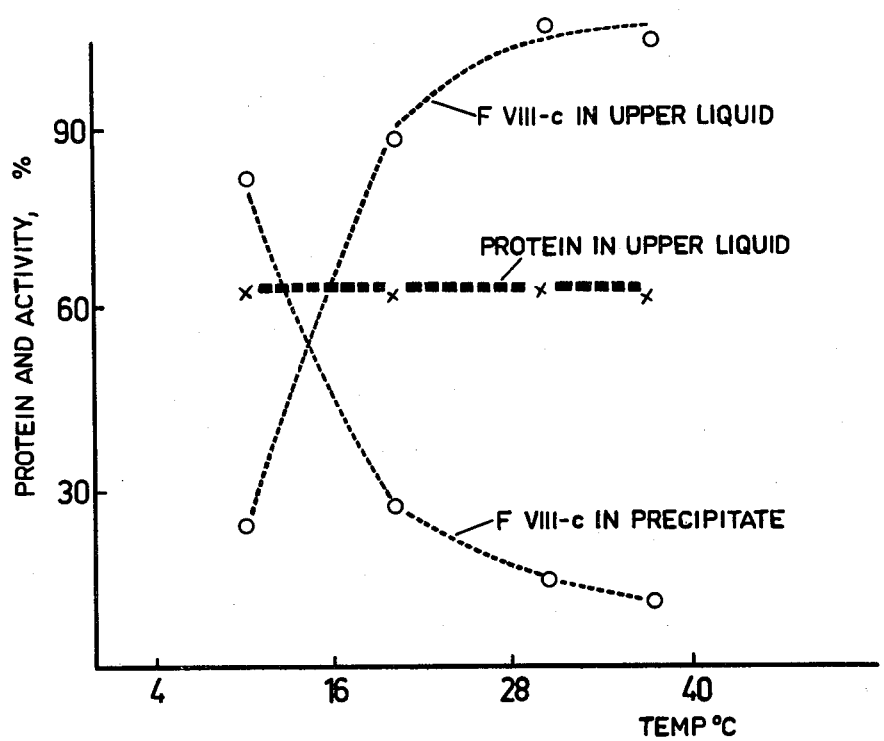
FIG. 2 shows the activity in the supernatant liquid, activity in the precipitate as well as protein in the supernatant liquid as a function of the temperature.
Figure 3:
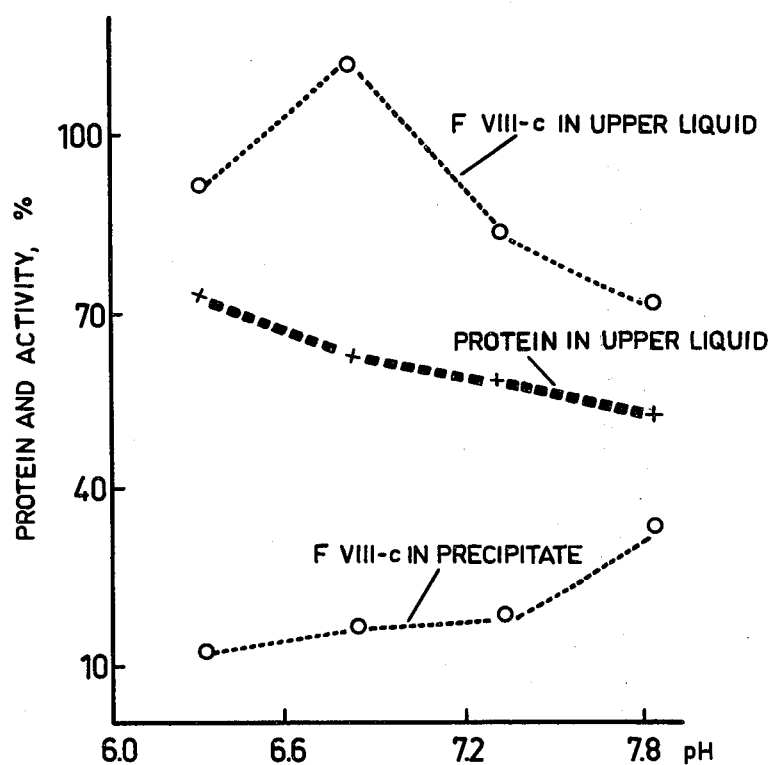
FIGS. 3 and 4 measure the same values as FIG. 2 but as a function of pH and ionic strength, respectively.
Figure 4:
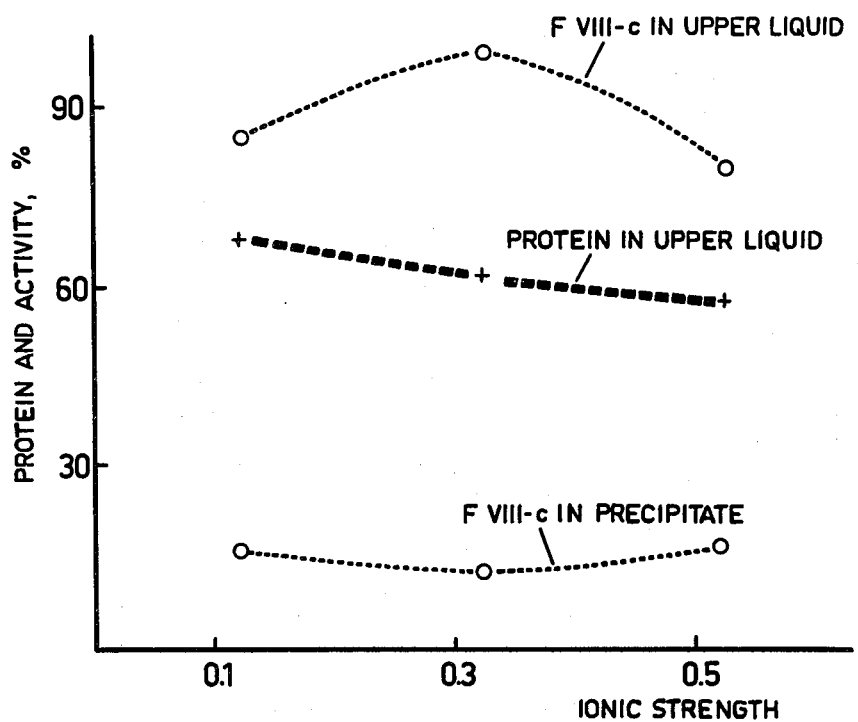

The invention is described more in detail in the following examples with reference to its use in the fractionation of blood plasma. In the examples, it is referred to the enclosed drawing, in which FIG. 1 shows protein and activity in the supernatant liquid and the specific activity as a function of the molarity of the glycine solution. FIG. 2 shows the activity in supernatant liquid and in precipitate and protein in the supernatant liquid as a function of the temperature. In FIGS. 3 and 4 the same quantities are shown as a function of pH and ionic strength, respectively.

EXAMPLE 1

Blood collected in citrate-phosphate-dextrose-adenine solution in an amount of 50 ml of citrate solution per 450 ml of blood. Blood cells are removed by centrifuging and plasma is sucked off. The plasma is fractionated with alcohol according to Cohn's fractionation method. Fraction I is washed in cold with glycine solution. The remaining precipitate, called fraction I-0, contains factor VIII complex and is dissolved in sodium citrate solution (pH 6.8) of 0.055 M to a protein concentration of about 2%. 8 parts of a buffer with a pH of 6.8 and containing varying amounts of glycine, 0.125 M NaCl and 0.025 M imidazole are added to 4 parts of this solution at room temperature. After stirring for 15 minutes the precipitate formed is removed by centrifugation at ambient temperature. The precipitate is dissolved in citrate solution. The precipitate as well as the supernatant liquid is analyzed in respect of activity of factor VIII:C (normalization of the coagulation time of plasma from persons with hemophilia A after recalcification) or with a commercial reagent (IMCO AB, Stockholm). The total protein is determined by means of Lowry's method. The results of this test appear from FIG. 1. As shown in the figure, considerable amounts of inert protein are precipitated from the solution of fraction I-0 at glycine concentrations of 1.1-2.2 M. When the glycine content increases over 2.2, additional precipitation of inert protein takes place, but considerable losses of factor VIII:C can occur from the supernatant liquid. At a glycine content of 1.5-2.0 M, the yield of factor VIII:C in the supernatant liquid is high, while the content of protein therein is much lower than in the original solution. The specific activity of the supernatant liquid is about 5 times higher than in he original solution at a glycine concentration of 2 M.

EXAMPLE 2

Blood and plasma are prepared in the way described in example 1. A counterpart of fraction I-0 is prepared by freezing of the factor VIII complex by adding polyethylene glycol 4000 in an amount of 1% to the plasma. The mixture is frozen at −70° C. At a slow thawing to +4° C. a precipitate called cryoprecipitate remains when all ice has melted. This precipitate contains between 60 and 90% of the factor VIII complex of the plasma. The precipitate is dissolved in 0.055 M sodium citrate solution (pH 6.8) to a protein content of about 3%. 10 parts of a buffer containing 3.0 M glycine, 0.125 M NaCl and 0.025 M imidazole (pH 6.8) are added to 5 parts of this solution at 10°, 20°, 30° and 37° C. The mixtures are brought to equilibrium at the different temperatures under stirring for 15 min. The precipitate formed is removed by centrifugation. Precipitate and supernatant liquid are analyzed as in example 1.

As is apparent from FIG. 2, the separation of the factor VIII complex from inert protein is highly dependent on the temperature of the glycine-protein mixture. At temperatures above 15° C., the main part of the factor VIII complex is found in the supernatant liquid, while at lower temperatures, the main part is in the precipitate.

EXAMPLE 3

The cryoprecipitate (see example 2) is dissolved in a 0.055 M citrate solution (pH 6.8) to a protein content of about 3%. 8 parts of buffer containing 3 M glycine, 0.125 M NaCl and 0.025 M imidazole, the pH of which has been adjusted to 6.3; 6.8; 7.3 and 7.8, respectively, are added dropwise to 4 parts of this solution. After stirring for 15 min at 30° C., the precipitate formed is removed by centrifugation and dissolved in citrate solution (pH 6.8). The supernatant liquid and the precipitate are analyzed according to example 1.

As is evident from FIG. 3, the differences in activity and yield at different pH are relatively small. An optimal separation of the factor VIII complex on behalf of supernatant liquid is obtained at approximately neutral pH.

EXAMPLE 4

10 parts of glycine-imidazole solution with a varying content of common salt (NaCl) were added dropwise to 5 parts of the cryoprecipitate (see examples 2 and 3). The composition of the different additional solutions is as follows:

(1) 3 M glycine, 0.025 M imidazole, pH 6.8; 2) 3 M glycine, 0.025 M imidazole, 0.3 M NaCl, pH 6.8; 3) 3 M glycine, 0.025 M imidazole, 0.6 M NaCl, pH 6.8.

After achieving equilibrium at 30° C. for 15 min the resulting precipitates are removed by centrifuging. The supernatant liquid and the precipitate are analyzed according to example 1.

The results are shown in FIG. 4. The variation in ionic strength between 0.1 and 0.5 has only a small effect on the distribution of the factor VIII complex in supernatant liquid and precipitate.

EXAMPLE 5

Fraction I-0 is dissolved in citrate solution (see example 1) to a protein content of about 2%. 10 parts of 3 M glycine containing 0.125 M NaCl and 0.025 M imidazole, pH 6.8, are added to 5 parts of the resulting solution. After stirring at 20° C. the precipitation (F I) is removed by centrifugation. The supernatant liquid (upper liquid I) is cooled to 4° C. Aqueous polyethylene glycol 6000 of 30% is then added to a final concentration of 10%. After stirring for 30 min at 4° C., the precipitate (F II) is removed from supernatant liquid (upper liquid II) by centrifuging. All supernatant liquids and precipitates are analyzed in the way described in example 1.

The distribution of the protein and the factor VIII complex in the different fractions is apparent from the following table 1. As is apparent from the table, the fraction I-0 is suitable as a starting material for fractionation. The results show, which is most important, that the factor VIII complex in the supernatant liquid can be concentrated by precipitation with polyethylene glycol after precipitation of inert protein with glycine.

TABLE 1

| Fraction | Vol. mls | Protein mg/ml | Total protein mg | Total protein % | VIII: C ϵ/ml | Total ϵ | VIII: C % | Specific activity ϵ/mg |
|---|---|---|---|---|---|---|---|---|
| F I-0 | 18 | 19.8 | 357 | 100 | 2.36 | 42.5 | 100 | 0.12 |
| Upper liquid I | 50 | — | — | — | 0.66 | 33.0 | 77.6 | — |
| F I | 19 | 11.5 | 219 | 61.3 | 0.49 | 9.3 | 21.6 | 0.04 |
| Upper liquid II | 73 | — | — | — | 0.14 | 10.2 | 24.0 | — |
| F II | 3.7 | 16.6 | 61 | 17.1 | 5.94 | 22.0 | 51.8 | 0.36 |

EXAMPLE 6

10 parts of solution containing 3 M glycine, 0.125 M NaCl and 0.025 M imidazole at pH 6.8 are added to 5 parts of solution of the cryoprecipitate (see example 4) at 20° C. After stirring for 10 min the precipitate (F I) formed is removed by centrifuging. The supernatant liquid (Upper liquid I) was cooled to 4° C. by centrifutation. The supernatant liquid (Upper liquid I) is cooled to 4° C., after which an aqueous solution of 30% of polyethylene glycol 6000 is added dropwise to a concentration of 6%. After stirring for 30 min the precipitate (F II) is removed from the supernatant liquid (upper liquid II) by centrifugation. All fractions are analyzed in the way described.

The results of the test appear from table 2. It is apparent from this that cryoprecipitate as well as fraction I-0 is suitable for this type of fractionation. The test also shows that the factor VIII complex, which according to the invention has been obtained in the supernatant liquid, can be concentrated by precipitation with polyethylene glycol.

TABLE 2

| Fraction | Vol. mls | Protein mg/ml | Total protein mg | Total protein % | VIII: C ϵ/ml | Total ϵ | VIII: C % | Specific activity ϵ/mg |
|---|---|---|---|---|---|---|---|---|
| Cryo | 18.5 | 26.4 | 488 | 100 | 5.57 | 103.0 | 100 | 0.21 |
| Upper liquid I | 53 | — | — | — | 1.72 | 91.2 | 88.5 | — |
| F I | 22.5 | 9.6 | 216 | 44.3 | 0.63 | 14.2 | 13.8 | 0.07 |
| Upper liquid II | 31 | — | — | — | 0.09 | 2 × 2.8 | 5.4 | — |
| F II (H) | 8.8 | 3.2 | 2 × 28.2 | 11.6 | 3.77 | 2 × 3.2 | 64.5 | 1.18 |

EXAMPLE 7

Cryoprecipitate (see example 2) is dissolved in 0.055 M citrate solution, pH 6.8, to a concentration of 3%. 3.3 parts of a solution containing 2.6 M glycine and 0.025 M imidazole, pH 7.3, are added to 1 part of this solution. The temperature of the mixture is simultaneously brought to 7° C. After the addition, the mixture is brought to equilibrium under stirring at 7° C. for 15 min. A precipitate (F I) is formed and removed by centrifugation. The supernatant liquid (Upper liquid I) is saved or analysis. The precipitate is dissolved in 0.055 M citrate solution, pH 6.8, at 30° C. to about the same volume as the original cryoprecipitate, after which 3.3 volumes of a solution containing 2.6 M glycine, 0.3 M NaCl and 0.025 M imidazole, pH 6.8, are added. Stirring is carried out at 30° C. for 20 min. The precipitate (F II) formed is removed by centrifugation. The supernatant liquid (Upper liquid II) is adjusted to pH 7.5 with a weak sodium hydroxide solution after cooling to 4° C. An aqueous solution of 30% polyethylene glycol 6000 is then added dropwise to a concentration of 6.5%. The mixture is stirred at 4° C. for 30 min, after which the precipitate formed is removed by centrifuging. The precipitate (F III) is dissolved in 0.055 M sodium citrate solution containing 0.055 M imidazole, pH 7.40. The supernatant liquid (Upper liquid II) is saved for analysis. All fractions are analyzed in the way described in example 1, and the results appear from the following table 3.

TABLE 3

| Fraction | Vol. mls | Protein mg/ml | Total protein mg | Total protein % | VIII: C ϵ/ml | Total ϵ | VIII: C % | Specific activity ϵ/mg |
|---|---|---|---|---|---|---|---|---|
| Cryo | 56 | 30.4 | 1702 | 100 | 4.29 | 240 | 100 | 0.14 |
| Upper liquid I | 228 | — | — | — | 0.25 | 57 | 23.8 | — |
| F I | 40 | 21.1 | 844 | 49.6 | 5.96 | 238 | 99.2 | 0.28 |
| Upper liquid II | 168 | — | — | — | 0.97 | 163 | 67.9 | — |
| F II | 30 | 23.5 | 705 | 41.4 | 0.49 | 15 | 6.3 | 0.02 |
| Upper liquid III | 198 | — | — | — | 0.04 | 8 | 3.3 | — |
| F III | 6.2 | 13.4 | 83 | 4.9 | 27.8 | 172 | 71.7 | 2.07 |

EXAMPLE 8

In the previous examples, the analyses of the factor VIII complex have only comprised factor VIII:C. In the following table 4 analyses of a factor VIII complex is shown, which has been isolated substantially in the way described in example 7.

TABLE 4

| Fraction | Prot. | VIII: C | VIII: CAG | F VIII: RAG | VIII: RCF | Spec. activity |
|---|---|---|---|---|---|---|
| Cryo | 100 | 100 | 100 | 100 | 100 | 0.15 |
| F III | 4 | 63 | 61 | 79 | 48 | 2.1 |

Remark: The factor VIII:C can be determined according to Nilsson et al: Acta Med. Scan. 159, 35 (1953) or according to Savidge et al: Thromb. Res. 16, 355 (1979). The factor VIII:CAG can be determined according to Lazarchick and Hoyer, J. Clin. Invest. 62, 1048 (1978).

It is apparent from the table that the complex, expressed in percent, contains the same concentration of coagulation factor VIII:C as of factor VIII:CAG. The content of factor VIII:RAG is somewhat higher and the content of factor VIII:RCF (lacking in v. Willebrand's disease) is somewhat lower than of factor VIII:C/CAG.

It is evident that products with a high solubility can be obtained in a good yield at fractionation with glycine according to the invention in combination with other fractionating processes. Furthermore, these preparations contain all the activities which in addition to F VIII:C are associated with the factor VIII complex. In comparison with plasma (the specific VIII:C activity of which is about 0.014 U/mg), the specific activity of the product will be 150–250 times greater, the yield from plasma under optimal conditions being 40–60%.

What we claim is:

1. A process for purifying and/or concentrating the factor VIII complex comprising the steps of:
   (1) dissolving a composition containing factor VIII complex together with impurities therein in glycine to form a solution of at least 1.5 M at a temperature of at least +15° C. and a pH of about 6.3–7.8 to form a solution containing factor VIII and a precipitate containing the impurities; and
   (2) recovering the supernatant fluid containing the factor VIII complex.

2. The process of claim 1 wherein the concentration of the glycine solution is 1.8 to 2.2 M.

3. The process of claim 1 wherein the temperature is between about 20° to about 40° C.

4. The process of claim 3 wherein the temperature is between about 20° to about 35° C.

5. A process for purifying and/or concentrating a composition containing the factor VIII complex, comprising the steps of:
   (1) dissolving a factor VIII-containing composition together with associated protein impurities in a solution of about 1.8 M to about 2.2 M glycine at a temperature of about 20° C. to about 35° C. at a pH of about 6.3 to 7.8, to form a solution of factor VIII in glycine and to form a precipitate of said protein, and
   (2) recovering the factor VIII complex rich in factor VIII:C/CAG and factor VIII-RAG/RCF, the recovered factor VIII complex having a specific activity about 150–250 times greater than that in plasma at a yield in the range of about 40 to 60%.

6. The process of claim 2 or 5 wherein the glycine concentration solution is about 2.0 M.

7. The process of claim 3 or 5 wherein the temperature is between about 25° and 37° C.

8. The process of claim 1 or 5 wherein the pH is about 6.5 to about 7.5.

9. The process of claim 8 wherein the pH is about 6.8.

10. The process of claim 4 or 5 wherein the temperature is about 25° C. to about 37° C.

11. The process of claim 1 or 5 wherein the ionic strength of the solution of step (1) is in the range of 0.1 to 0.5.

12. The process of claim 1 or 5 wherein the composition containing the factor VIII used as the starting materials in step (1) is a cryoprecipitate or from Cohn's fraction I-0.

13. The process of claim 1 or 5 including the additional step of:
   (3) adding polyethylene glycol to the solution recovered in step (2) thereby precipitating the purified and concentrated factor VIII from said solution.

* * * * *